United States Patent
Eikanas

(10) Patent No.: US 6,663,579 B2
(45) Date of Patent: Dec. 16, 2003

(54) DEVICE FOR REDUCING HAND CONTRACTURE

(76) Inventor: Joanna Eikanas, 5886 Bufkin Ct., San Jose, CA (US) 85123

( * ) Notice: Subject to any disclaimer, the term of this patent is extended or adjusted under 35 U.S.C. 154(b) by 297 days.

(21) Appl. No.: 09/826,277

(22) Filed: Apr. 4, 2001

(65) Prior Publication Data

US 2002/0147074 A1 Oct. 10, 2002

(51) Int. Cl.[7] .............................. A63B 23/16; A61F 5/10
(52) U.S. Cl. .............................. 601/40; 482/49; 482/91; 482/124; 602/21
(58) Field of Search .............................. 482/44, 49, 91, 482/124; 601/40; 602/21

(56) References Cited

U.S. PATENT DOCUMENTS

| | | | | |
|---|---|---|---|---|
| 2,077,202 A | * | 4/1937 | Barrie | 119/14.22 |
| 3,835,472 A | * | 9/1974 | Duggins | 2/161.7 |
| 4,496,151 A | * | 1/1985 | Tureaud | 473/59 |
| 4,558,694 A | * | 12/1985 | Barber | 602/21 |
| 4,711,445 A | * | 12/1987 | Whitehead | 482/49 |
| 5,005,824 A | * | 4/1991 | Eichel | 482/44 |
| 5,135,455 A | * | 8/1992 | King et al. | 482/108 |
| 5,383,827 A | * | 1/1995 | Stern | 482/47 |
| 5,437,620 A | * | 8/1995 | Shelly | 602/21 |
| 6,482,168 B1 | * | 11/2002 | Betcher | 602/21 |
| 6,503,216 B1 | * | 1/2003 | Thibodo, Jr. | 602/21 |

* cited by examiner

Primary Examiner—Nicholas D. Lucchesi
Assistant Examiner—Victor K. Hwang
(74) Attorney, Agent, or Firm—David B. Waller & Associates

(57) ABSTRACT

In accordance with the present invention a device for reducing hand contracture resulting from injury or trauma is disclosed comprising at least one column comprising a plurality of blocks, the plurality of blocks having at least one attachment means enabling the plurality of blocks to be assembled into at least one column, and a securing band able to encircle a hand when the at least one column is positioned at a base of the fingers on the palm and extending toward the fingers of the hand. In addition methods are disclosed for reducing hand contracture using the device of the present invention as well as kits comprising the components of the device of the present invention for assembly by the user.

11 Claims, 2 Drawing Sheets

FIG. 1
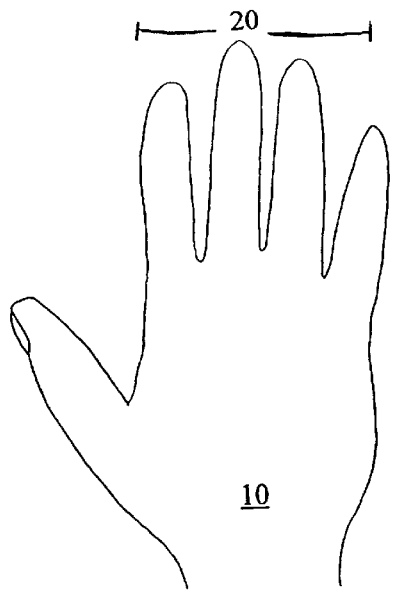
FIG. 2
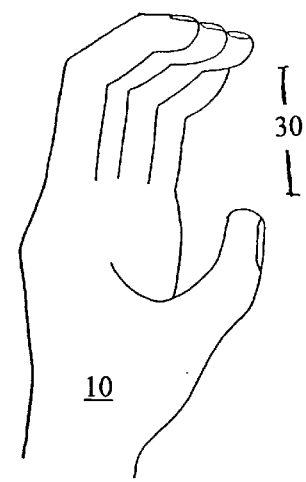
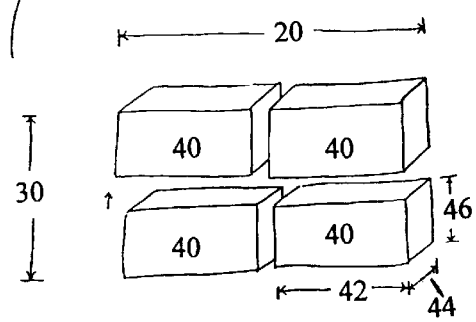
FIG. 3
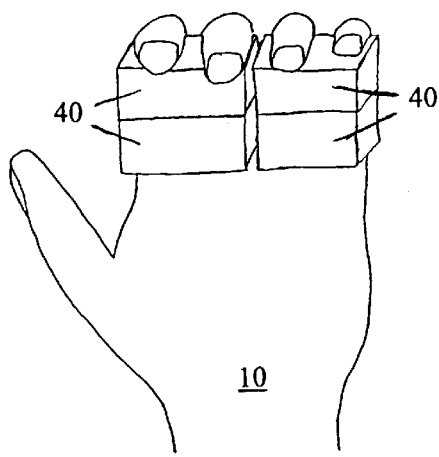
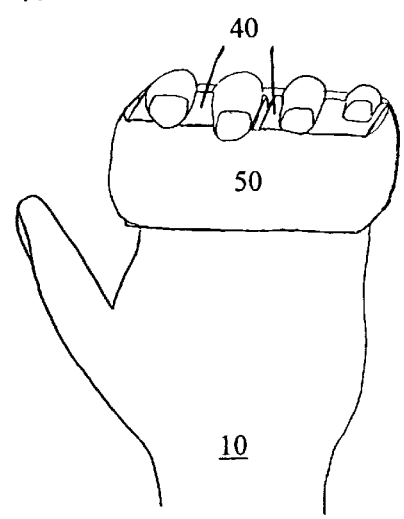
FIG. 4
FIG. 5

DEVICE FOR REDUCING HAND CONTRACTURE

TECHNICAL FIELD

The present invention relates generally to medical devices for treating an injured hand, and more particularly to devices for reducing hand contracture resulting from injury or trauma.

BACKGROUND OF THE INVENTION

Hand contracture may result from injury or trauma and is an involuntary tightening of the muscles and tendons in the hand and fingers primarily due to atrophy causing the hand to close. If left untreated, the hand often continues to tighten forming a permanent fist. When this occurs, the internal portions of the hand such as the palm and the region between the fingers become difficult to clean, and the fingernails difficult to trim. If the hand contracture is severe, the fingernails can puncture the palm creating a high risk of infection. Treatment usually involves extending the muscles and tendons mechanically using a variety of devices and often incorporates stretching exercises. Those suffering from fracture, soft tissue injury, stroke, arthritis, and neurological disorders are at risk for hand contracture.

Many existing devices for hand contracture treat the hand and fingers as a single unit. Consequently, all fingers are treated as if each was equally tightened. However, hand contracture can often effect the fingers individually and to varying degrees. Therefore, treating the entire hand as single unit is not preferred and often causes the fingers with more flexibility to worsen until all fingers are equally contracted.

Generally, devices used to treat hand contracture involve a rigid splint platform secured to either the topside or the bottom side of the patient's arm. The former generally wrap over the top of the hand and pull the fingers outward. The latter generally provide a rigid platform along the arm extending to the palm to prevent further contracture of the fingers or incorporate a component such as an air bladder to extend the fingers. However, wearing a device that incorporates a rigid splint platform limits the movement of the wrist and can be uncomfortable for the patient. Moreover, the limited wrist movement makes daily routines such as dressing difficult.

Consequently, a device for reducing hand contracture resulting from injury or trauma is needed that allows individual adjustment of the fingers, does not restrict wrist movement, and provides comfort during use.

SUMMARY OF THE INVENTION

The object of the present invention is to provide a device that reduces hand contracture by allowing the individual adjustment of the fingers without restricting wrist movement.

In accordance with the present invention a device for reducing hand contracture is disclosed comprising at least one column comprising a plurality of blocks, the plurality of blocks having at least one attachment means enabling the plurality of blocks to be assembled into at least one column, and a securing band able to encircle a hand when the at least one column is positioned at a base of the fingers on the palm and extending toward the fingers of the hand. The attachment means may be any known to those skilled in the art that may withstand the force exerted from a contracted hand such as interlocking surfaces, tongue and groove, and pins. The interlocking surface may further comprise a snap or a twisting lock.

In one embodiment of the invention the blocks may further comprise an aperture located about the center of two parallel sides of the blocks, about perpendicular to said parallel sides, and extending through the blocks such that the apertures are in contact with one another when the blocks are attached into a column. When the blocks comprise an aperture, the device may further comprise a stabilizing rod. Furthermore, the columns may be connected to one another using any affixing means known to those skilled in the art such that the columns are not permanently connected such as a snap or a joining rod.

In another embodiment of the invention the blocks have a generally rectangular shape having a length, width, and height. The length may be from about one half inch to about one and one half inch, the width may be from about one quarter inch to about one inch, and the height may be from about one quarter inch to about one inch. Moreover, the blocks may be constructed of a semi-rigid polymer.

In one aspect of the present invention a kit comprising a device for reducing hand contracture resulting from injury or trauma is disclosed comprising a plurality of blocks of variable sizes suitable for use with different size hands, and at least one securing band. The kit may further comprise at least one stabilizing rod and may further comprise at least one joining rod.

In another aspect of the present invention, a method for reducing hand contracture is disclosed utilizing the disclosed device comprising attaching the plurality of blocks to form at least one column, placing the column or columns at the base of the fingers on the palm of the hand such that the column or columns are in contact with the fingers and such that the column or columns extend toward the fingertips, and wrapping the securing band around the hand such that the column or columns are anchored within the hand. Furthermore, the method may further comprise inserting a stabilizing rod through the aperture of the blocks extending the stabilizing rod through the column. If two or more columns are used, the method may further comprise affixing two or more columns together prior to placing the device on the hand.

BRIEF DESCRIPTION OF THE DRAWINGS

FIG. 1 is a palm view showing the width dimension of a hand;

FIG. 2 is a side view showing the height dimension of a hand;

FIG. 3 is a perspective view of two assembled columns of two blocks of the present invention;

FIG. 4 is a view of the columns of FIG. 3 positioned in a hand;

FIG. 5 is a view of the columns of FIG. 3 secured in position with a securing band;

DETAILED DESCRIPTION OF THE INVENTION

Figure 6:
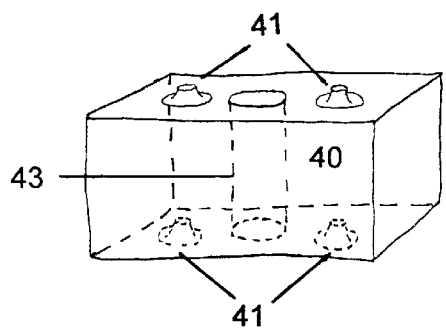
FIG. 6 is a perspective view of a block having attachment means and aperture.
Figure 7:
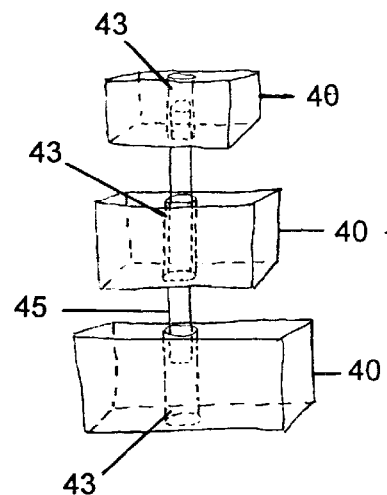
FIG. 7 is a perspective view of three variable size blocks having apertures and a stabilizing rod.
Figure 8:
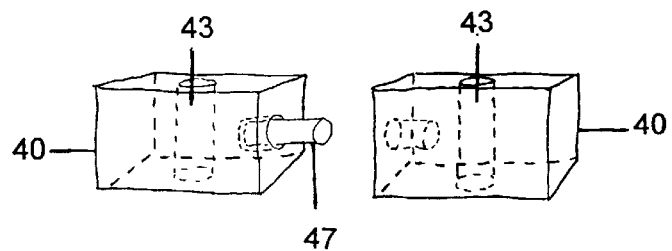
FIG. 8 is a perspective view of two columns of one block having apertures and a joining rod.

A device for reducing hand contracture resulting from injury or trauma comprising at least one column comprising a plurality of blocks, the plurality of blocks having at least one attachment means enabling the plurality of blocks to be assembled into at least one column, and a securing band able to encircle a hand when the at least one column is positioned at a base of the fingers on the palm and extending toward the fingers of the hand.

The blocks may be constructed in a variety of shapes that when used separately, or assembled into a column, conform to the base of the fingers. Preferably the shape is generally rectangular having a length, width, and height. The length maybe from about one half inch to about one and one half inch, the width maybe from about one quarter inch to about one inch, and the height maybe from about one quarter inch to about one inch.

The blocks may be constructed in a variety of sizes such that they conform to different size hands. Smaller blocks may be desirable for smaller hands or a more severely contracted hand. The length, (42) see FIG. 3, of the blocks (40) may be less than or generally equal to one half the width of a hand allowing the placement of at least two blocks adjacent to one another lengthwise across the hand. The height, (46) see FIG. 3, may be less than or approximately equal to one half the length of the fingers. The width (44) see FIG. 3, maybe from about one-third to about two-thirds the length of the finger. Preferably, the blocks (40) are constructed in assorted sizes as described such that the blocks may be chosen according to the size of the user's hand and according to the degree of hand contracture. Consequently, an assembled column may have two or more blocks of different sizes.

Each block may further comprise one or more grooves along the surface to conform to the contours of the hand. The surface grooves may be generally complimentary to the shape of one or more fingers, the base of the fingers, or the region between the fingers. Grooves complimentary to the finger or base of the fingers allow the device to fit more comfortably in the hand and assist in reducing movement of the column when in position within the hand. Blocks that have a groove complimentary to the region between the fingers assist in treating the hand by spreading the fingers as well as reducing movement once the assembled column is in place. Moreover, blocks may incorporate different grooves depending on the blocks intended placement within the column. For example, a block intended for the base of a column may have a groove generally complimentary to the base of the fingers, and a block intended for the top of the column may have a groove complimentary to the upper finger. In addition, the base and top blocks may further comprise grooves that conform to the length of the finger.

The blocks may be constructed from any semi-rigid material known to those skilled in the art such that the column may retain the general shape while allowing minimal compression with respect to the height for comfort. The material selected should be able to withstand the force exerted by a hand suffering from contracture. More particularly, the blocks should not be made of a material that deforms due to hand contracture pressure to the extent that treatment in ineffective while at the same time providing comfort. Preferably the blocks are constructed of putty elastomer.

The blocks may be attached to form a column in anyway known to those skilled in the art such as interlocking surfaces, tongue and groove, or pins such that the blocks do not separate once the columns are positioned in the hand and the hand is wrapped with a securing band. The attachment means preferably does not permanently affix the blocks yet must be able to withstand the force exerted by a hand suffering from contracture and from the force exerted by the securing band. More specifically, an interlocking surface may be any interlocking surface known to those skilled in the art such as a snap or a twisting lock. When the attachment means is a pin, the pin may lock within the block to secure the pin in place. Furthermore, the attachment means may be cast as a single unit with the block or may be cast separately then affixed to the block.

Each block may further comprise an aperture located about the center of two parallel sides of the block and extending through the block such that when the blocks are assembled into a column the apertures are in contact with one another. The aperture may be any shape such as round, oval, generally square, or star shaped. Preferably the aperture is round.

When the blocks comprise an aperture, the device may further comprise a stabilizing rod shaped having a shape complimentary to the aperture. The stabilizing rod should be a length suitable for extending through an attached column of blocks and may be tapered for easier insertion into the aperture. Stabilizing rods may be cast in lengths for use with columns of different heights and may be constructed of any material known to those skilled in the art that provides structural support to the column. Preferably the stabilizing rods are constructed of metal, graphite, carbon fiber, or a semi-rigid polymer plastic.

In another embodiment of the present invention the blocks may further comprise an affixing means allowing two or more columns to be joined together. The affixing means may be any means known to those skilled in the art that can reversibly connect the columns to one another such as for example a snap or a joining rod. When the affixing means is a joining rod, it may be constructed of any rigid material such as metal or a flexible material such as graphite, carbon fiber or a rubber composite. Preferably the affixing means is a joining rod constructed of a rubber composite. A joining rod may be provided in any number of shapes such as, for example, round, oval, generally square, or star shaped and should have a length about equal to or less than the length of a block. When a joining rod is used, the blocks should have apertures complimentary to the shape of the joining rod. Preferably the shape and size of the joining rod and its corresponding aperture are different from that of the stabilizing rod and its corresponding aperture to prevent the caretaker or user from inserting the rods into the incorrect apertures. The joining rod apertures are located about the center of two parallel sides of a block and extend generally perpendicular to the attachment means but not intersect a stabilizing rod aperture.

The securing band may be constructed of a variety of materials known to those skilled in the art such that the support band may wrap around the hand securing the columns at the base of the fingers in the palm of the hand. The material may be elastic or static, preferably the securing band is constructed of an elastic material to allow it to conform more tightly to the hand and device. The support band may be self-adjusting or may require the caretaker to adjust the band. Self-adjusting fastening means that may be utilized with the securing band include but are not limited to snaps, Velcro™, or tape. A caretaker may be required to assemble the securing band by cutting the band to a desired length and affixing a fastening means to the band. Alternatively the band may be provided in a length with a fastening means that will adjustable fit a majority of hands. Moreover, there may be two or more constructions of the support band having different widths so that a narrower support band is used with smaller columns, for example a width of about 1 inch to about 3 inches, and a wider with larger columns for example a width of about 3 to about 6 inches. Preferably one securing band is constructed having a width of about 2 to about 4 inches, that may be able to be folded over width wise to have a width of about one inch to about two inches.

In still another embodiment of the present invention a kit is provided comprising a plurality of blocks of variable sizes suitable for use with different size hands and a support band. The kit may further comprise one or more stabilizing rods and may comprise one or more joining rods.

In yet another embodiment of the present invention a method for reducing hand contracture is provided comprising attaching a plurality of blocks to form at least one column, placing the column or columns at the base of the fingers on the palm of the hand such that the column or columns are in contact with the fingers and such that the column or columns extend toward the fingertips, and wrapping a securing band around the hand such that the column or columns are secured within the hand.

When this method is performed it may further comprise inserting a stabilizing rod through an aperture in the blocks and extending the stabilizing rod through the column. Additionally, the method may further comprise affixing two or more columns together prior to placing the device in and securing the device to the hand. Assistance may be desired to hold the affixed columns in place while the securing band is wrapped around the hand.

When these methods are performed and prior to assembly of the device, the caretaker assesses the size of the hand (particularly the width (20) of the hand (10), see FIG. 1) and the degree of contracture to determine the size of the column necessary (in particular the distance between the contracting fingers and the base of the fingers near the palm (30) see FIG. 2) and therefore the number of blocks (40) to be used. For example, FIG. 3 shows the construction of a device for a hand contracture that will accept two columns of two blocks (40) each. Alternatively, a hand (10) suffering severe contracture may be unable to accept a column of two attached blocks and may only be able to accept one block (40). In this instance, the caretaker should insert columns consisting of one block (40) until the hand opens sufficiently for insertion of a column comprising two blocks. The columns are positioned in the effected hand (10), see FIG. 4, and a securing band (50) is placed around the hand (10) to secure the device in place, see FIG. 5. Thus, the caretaker may evaluate the effectiveness of the blocks (40) over time and adjust the column height (30) accordingly. Once the hand (10) begins to open, the column's height (30) may be increased by attaching additional blocks (40). This method is repeated until the hand is fully opened.

The method may be different depending on the injury or trauma. For example, a hand suffering less contracture along the index and middle finger may require a larger column placed at the base between the first and index fingers than the remaining fingers. In this case, the caretaker may also choose to wrap the support band around each column and corresponding fingers individually. Additionally, if the thumb is affected, the method may further comprise placing a block between the thumb and the palm and wrapping the thumb and column or block as a separate unit.

What is claimed is:

1. A device for reducing hand contracture resulting from injury or trauma comprising:
   a. at least one column comprising a plurality of blocks, said plurality of blocks having at least one attachment means enabling said plurality of blocks to be assembled into at least one column and an aperture located about the center of two parallel sides of and extending through said plurality of blocks about perpendicular to said sides and wherein said aperture is in contact with another said aperture when said plurality of blocks are assembled into a column, wherein said plurality of blocks further comprise an affixing means perpendicular to said attachment means such that said at least one column may be connected to another at least one column; and
   b. a securing band able to encircle a hand when said at least one column is positioned at a base of the fingers on the palm and extending toward the fingers of said hand.

2. A device for reducing hand contracture resulting from injury or trauma according to claim 1 further comprising at least one stabilizing rod able to be fitted through said aperture.

3. A method for reducing hand contracture utilizing a device according to claim 2 comprising:
   a. attaching said plurality of blocks to form at least one column;
   b. inserting said at least one stabilizing rod into said aperture and extending said at least one stabilizing rod through said at least one column;
   c. placing said at least one column at the base of the fingers on the palm of a hand such that said at least one column is in contact with at least two fingers and extends toward the fingertips; and
   d. wrapping said securing band around said hand such that said at least one column is secured within said hand.

4. A kit comprising a device for reducing hand contracture resulting from injury or trauma according to claim 2 further comprising:
   a. said plurality of blocks having variable sizes suitable for use with different size hands;
   b. said securing band; and
   c. at least one stabilizing rod.

5. A kit comprising a device for reducing hand contracture resulting from injury or trauma according to claim 2 further comprising:
   a. said plurality of blocks having variable sizes suitable for use with different size hands;
   b. said securing band;
   c. at least one stabilizing rod; and
   d. at least one joining rod.

6. A device for reducing hand contracture resulting from injury or trauma according to claim 1 wherein said plurality of blocks further comprise a generally rectangular shape having a length, width, and height wherein said length is about one half inch to about one and one half inch, said width is about one quarter inch to about one inch, and said height is about one quarter inch to about one inch.

7. A device for reducing hand contracture resulting from injury or trauma according to claim 1 wherein said affixing means is a joining rod.

8. A kit comprising a device for reducing hand contracture resulting from injury or trauma according to claim 7 further comprising:
   a. said plurality of blocks having variable sizes suitable for use with different size hands;
   b. said securing band; and
   c. at least one joining rod.

9. A kit comprising a device for reducing hand contracture resulting from injury or trauma according to claim 7 further comprising:

a. said plurality of blocks having variable sizes suitable for use with different size hands;
b. said securing band;
c. at least one stabilizing rod; and
d. at least one joining rod.

10. A method for reducing hand contracture utilizing a device according to claim 1 comprising:
   a. attaching said plurality of blocks into at least two columns;
   b. affixing together said at least two columns;
   c. placing said affixed columns at the base of the fingers on the palm of hand such that said affixed columns are in contact with at least four fingers and extend towards the fingertips; and
   d. wrapping said support band around said hand such that said two or more columns are secured within said hand.

11. A method for reducing hand contracture utilizing a device according to claim 1 comprising:
   a. attaching said plurality of blocks into at least two columns;
   b. inserting said at least one stabilizing rod into at least one aperture and extending at least one stabilizing rod through at least one of said at least two columns;
   c. affixing together said at least two columns;
   d. placing said affixed columns at the base of the fingers on the palm of hand such that said affixed columns are in contact with at least four fingers and extend towards the fingertips; and
   e. wrapping said support band around said hand such that said two or more columns are secured within said hand.

* * * * *